(12) United States Patent  
Qiu

(10) Patent No.: US 7,329,537 B2
(45) Date of Patent: Feb. 12, 2008

(54) MICRO-PATTERN EMBEDDED PLASTIC OPTICAL FILM DEVICE FOR CELL-BASED ASSAYS

(75) Inventor: Jean Qiu, Andover, MA (US)

(73) Assignee: Nexcelom Bioscience, LLC, Lawrence, MA (US)

( * ) Notice: Subject to any disclaimer, the term of this patent is extended or adjusted under 35 U.S.C. 154(b) by 46 days.

(21) Appl. No.: 10/825,883

(22) Filed: Apr. 17, 2004

(65) Prior Publication Data

US 2005/0208467 A1 Sep. 22, 2005

Related U.S. Application Data

(60) Provisional application No. 60/463,262, filed on Apr. 17, 2003.

(51) Int. Cl.
*C12M 1/34* (2006.01)
(52) U.S. Cl. .............. 435/288.3; 435/288.4; 435/288.7; 435/305.1; 435/305.2; 359/397; 359/398; 422/102
(58) Field of Classification Search ............. 435/305.2, 435/305.3, 288.3, 288.4, 305.1; 359/397, 359/398
See application file for complete search history.

(56) References Cited

U.S. PATENT DOCUMENTS

| | | | |
|---|---|---|---|
| 4,374,077 A | 2/1983 | Kerfeld | |
| 4,415,405 A | 11/1983 | Ruddle et al. | |
| 4,997,266 A | 3/1991 | Mitchell | |
| 5,175,030 A | 12/1992 | Lu et al. | |
| 5,712,161 A * | 1/1998 | Koezuka et al. | 435/382 |
| 5,812,312 A * | 9/1998 | Lorincz | 359/397 |
| 6,597,500 B1 * | 7/2003 | Burke et al. | 359/397 |
| 2002/0072113 A1 * | 6/2002 | Barbera-Guillem et al. | 435/305.1 |
| 2004/0145805 A1 | 7/2004 | Qiu | |

FOREIGN PATENT DOCUMENTS

| | | |
|---|---|---|
| DE | 3732142 A1 * | 4/1989 |
| DE | 19952139 | 10/1999 |
| DE | 19952139 C1 * | 12/2000 |
| JP | 11075819 A * | 3/1999 |
| JP | 2001017157 A * | 1/2001 |

OTHER PUBLICATIONS

Bradke, F. et al.; "Differentiated Neurons Retain the Capacity to Generate Axons from Dendrites"; Current Biology, vol. 10, pp. 1467-1470; Nov. 2000.

* cited by examiner

*Primary Examiner*—William H. Beisner
(74) *Attorney, Agent, or Firm*—Guerin & Rodriguez, LLP

(57) ABSTRACT

In the present invention, a micro-pattern embedded optical film for cell-based assays is described. The optical film contains micro-patterns in the form of geometric shapes, such as lines and curves, and numbers and letters. Furthermore, the optical film contains a coordinate system that allows identification of each location on the optical film for cell-based assays, including cell growth, identification, and measurements under an optical microscope. Furthermore, an apparatus with the micro-pattern embedded optical film and a supporting part is described. Methods for making the optical film and apparatus are disclosed. A method for performing cell-based assays using the optical film or apparatus is shown.

16 Claims, 16 Drawing Sheets

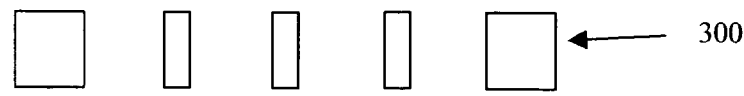
Fig. 14 (a)
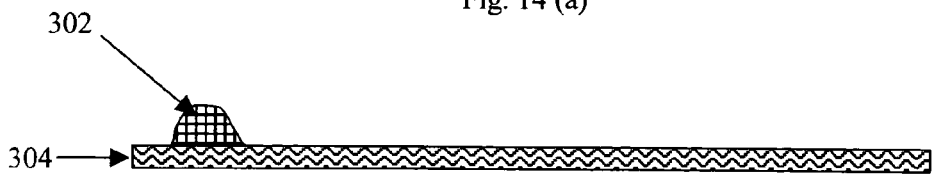
Fig. 14 (b)
Fig. 14 (c)
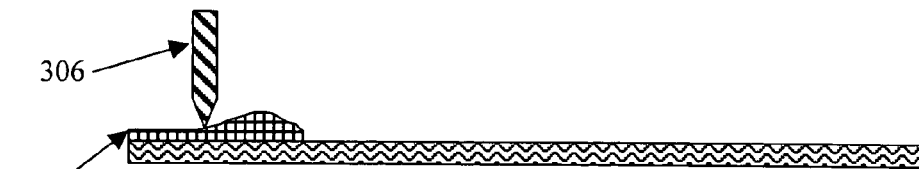
Fig. 14 (d)
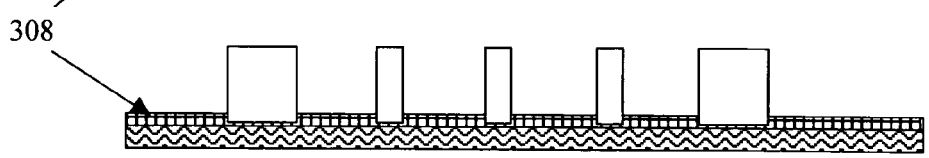
Fig. 14 (e)
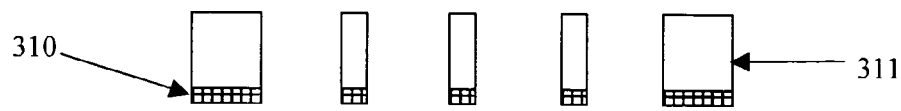
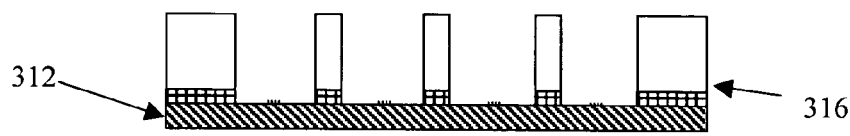
Fig. 14 (f)
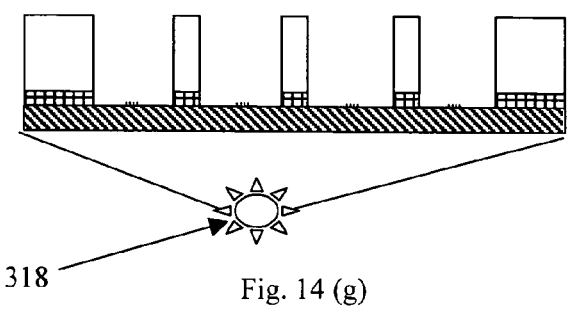
Fig. 14 (g)

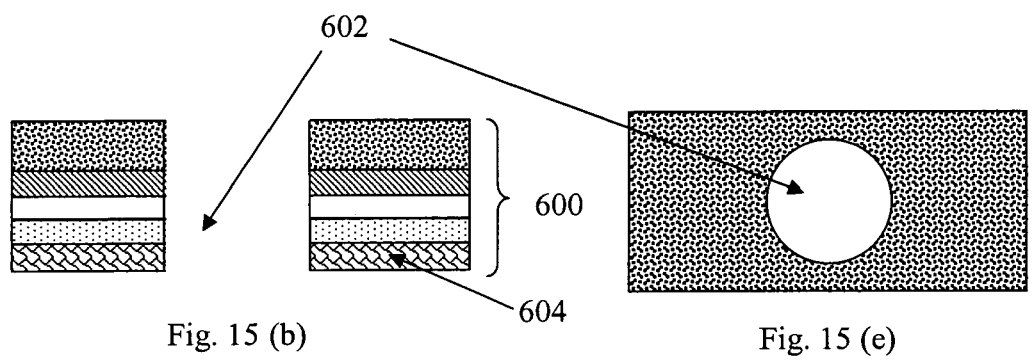
Fig. 15 (b)
Fig. 15 (e)
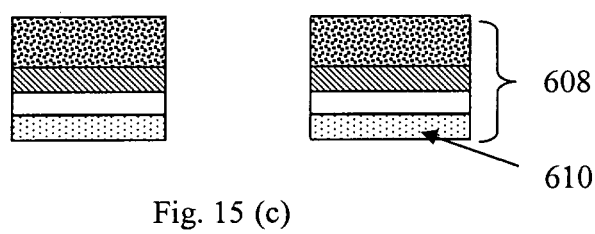
Fig. 15 (c)
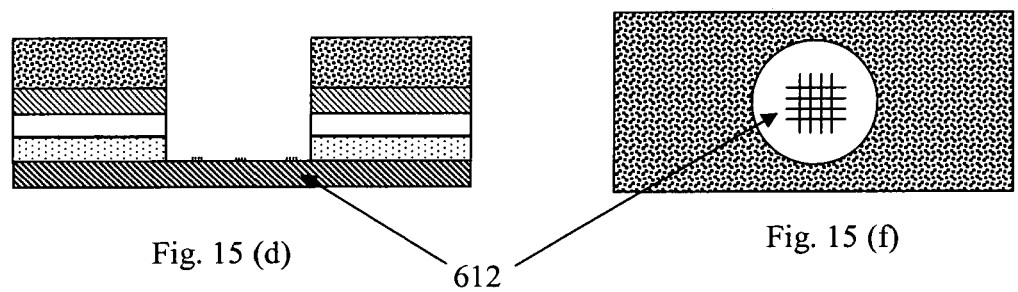
Fig. 15 (d)
Fig. 15 (f)

MICRO-PATTERN EMBEDDED PLASTIC OPTICAL FILM DEVICE FOR CELL-BASED ASSAYS

CROSS-REFERENCE TO RELATED APPLICATIONS

This application claims priority to U.S. Provisional Patent Application Ser. No. 60/463,262, filed Apr. 17, 2003. The application is related to commonly owned application Ser. No. 10/760,000, filed Jan. 16, 2004, pending.

OTHER REFERENCES

Bradke, F., et al., "Differentiated neurons retain the capacity to generate axons from dendrites", Current Biology, Vol. 10, pp. 1467-1470, November 2000.

BACKGROUND OF THE INVENTION

This invention is in the field of biological research and drug discovery, specifically in cell-based assays.

Tissue culture of plant and animal cells in vitro allows researchers to identify critical chemical factors affecting the functions of cells, such as spreading, morphology, motility, and differentiation. Currently, majority of tissue culture experiments are performed on flat surfaces of plastic or glass vessels. The measurements are obtained from large groups of cells without the ability to identify, to monitor and to measure an individual cell. The results are an average of the entire cell population.

In order to monitor and to measure a single cell, a tissue culture vessel is typically placed on a microscope stage. The tissue culture vessels remains on the stage until the measurement is complete, while the duration of the experiment may be from hours to days. The throughput of this method is extremely low. To increase the throughput, instruments with high precision motion control are designed to locate the tissue culture vessel to the same location repeatedly. Between each measurement, the tissue culture vessel is placed in an incubator while the microscope performs other measurements. Instruments of this type are typically complex and expensive.

Another method used to identify individual cells is using tissue culture vessels with embedded patterns as identification marks. U.S. Pat. No. 4,415,405 described a method for engraving a grid pattern on microscope slides and slips. The disclosed method employs a photographic technique to create a grid pattern image in a photo-resist coating on the slide or slip. Development of photo-resist and subsequent etching of glass produce the engraved slide or slip. A limitation of this technique is that engraved slides and slips are expensive to make with this method. In addition, the glass surface also limits the kind of cells that can be grown, since some cells do not grow on glass.

One objective of the current invention is to provide a tissue culture vessel that is capable of direct identification and measurement of individual cell activities, and also the tissue culture vessel can be fabricated with an inexpensive method.

Creation of microscopic features in plastic material from a molding surface has been described in the prior art. Process of making optical disks with microscopic features using photo-polymerizable materials is disclosed in U.S. Pat. No. 4,374,077. Microstructure-bearing composite plastic articles and method of making said articles are disclosed in U.S. Pat. No. 5,175,030. Grid lines directly molded onto the plastic for cell counting is disclosed in U.S. Pat. No. 4,997,266. U.S. patent application Ser. No. 10/760,000 disclosed a novel cell counting device with embedded grid lines.

SUMMARY OF THE INVENTION

The first objective of the present invention is to provide a micro-pattern embedded optical film that supports growth, identification and measurement of cells.

The micro-patterns that are embedded in the optical film may have shapes that are straight, curved, or of other geometrical shapes. The micro-patterns that are embedded in the optical film may contain lines that form grids. The micro-patterns that are embedded in the optical film may include numbers, letters, and combinations of numbers and letters. The dimensions of the micro-patterns may range from sub-micron to several millimeters.

Furthermore, the micro-patterns that are embedded in the optical film may contain a coordinate system wherein each location may be identified by a set of numbers or letters or combination of letters and numbers that are embedded in the optical film. The purpose for the coordinate system is to identify locations of any given area on the optical film.

The use of the micro-pattern embedded optical film is typically for observation under an optical microscope. For this usage, the purpose for the coordinate system is to allow the user to return to the same spot on the optical film for observation under a microscope.

The micro-pattern embedded optical film may have two sides: a first side that contains embedded micro-patterns, and a second side that contains no micro-patterns. The first side and the second side may both contain micro-patterns. Cells can be grown on either the first side or the second side. Furthermore, cells may grow on both the first side and the second side.

The micro-pattern embedded optical film is typically used in conjunction with tissue culture vessels, such as tissue culture dishes, which contain a micro-pattern embedded optical film and a liquid media necessary for cell growth.

The second objective of the present invention is to provide a method of using the micro-pattern embedded optical film for cell-based assays. The cell-based assays that may be performed with the micro-pattern embedded optical films include experimentation with cell functions including spreading, morphology, motility, and differentiation.

The third objective of the present invention is to provide an apparatus that contains micro-pattern embedded optical film and other necessary supporting components for cell-based assays.

The micro-pattern embedded optical film may be incorporated into tissue culture vessels by combining the micro-pattern embedded film with supporting components. The supporting components provide mechanical strength for handling, both manually and robotically. They also provide liquid containment for chemical reagents necessary for the cell-based assays.

On the apparatus that contains micro-pattern embedded optical film, there may be multiple assay locations with embedded micro-patterns.

The fourth objective of the present invention is to provide a method to fabricate the apparatus that consists of micro-pattern embedded optical film and other necessary supporting components for cell-based assays.

The micro-pattern embedded optical film may be fabricated with a flexible plastic film as a substrate. The micro-patterns may be formed on the substrate with a micro-replication technique. Furthermore, the micro-replication technique may consist of steps including casting an uv-curable material onto a mold with the negative of the desired micro-pattern, laminate a plastic film onto the mold, cure the uv-curable material with uv light irradiation, and removing the plastic film from the mold.

The support components may be manufactured from various materials with various techniques, such as injection molded plastic, die-cut or laser cut sheet material with sufficient liquid holding capacity. The material used for making the supporting components may be plastic, glass, or metal.

A supporting component may be made as a separate part and bonded to a micro-pattern embedded optical film. The technique of bonding may employ a pressure sensitive adhesive (PSA) or a thermoset adhesive such as a uv-curable adhesive.

The supporting components may also be formed directly onto the micro-pattern embedded optical film in pre-determined areas, using a material deposition technique such as stenciling or masked printing. The pre-determined areas may be separating locations where cell growth occurs.

BRIEF DESCRIPTION OF THE DRAWINGS

The invention will best be understood by reference to the accompanying drawings, wherein:

FIGS. 14(a)-14(g) illustrate a method of attaching a micro-pattern embedded optical film to a liquid handling part, using a UV curable bonding material.

These figures, which are idealized and are not to scale, are intended to be merely illustrative and non-limiting.

DETAILED DESCRIPTION OF THE INVENTION

Micro-Pattern Embedded Optical Film

Figure 1A:
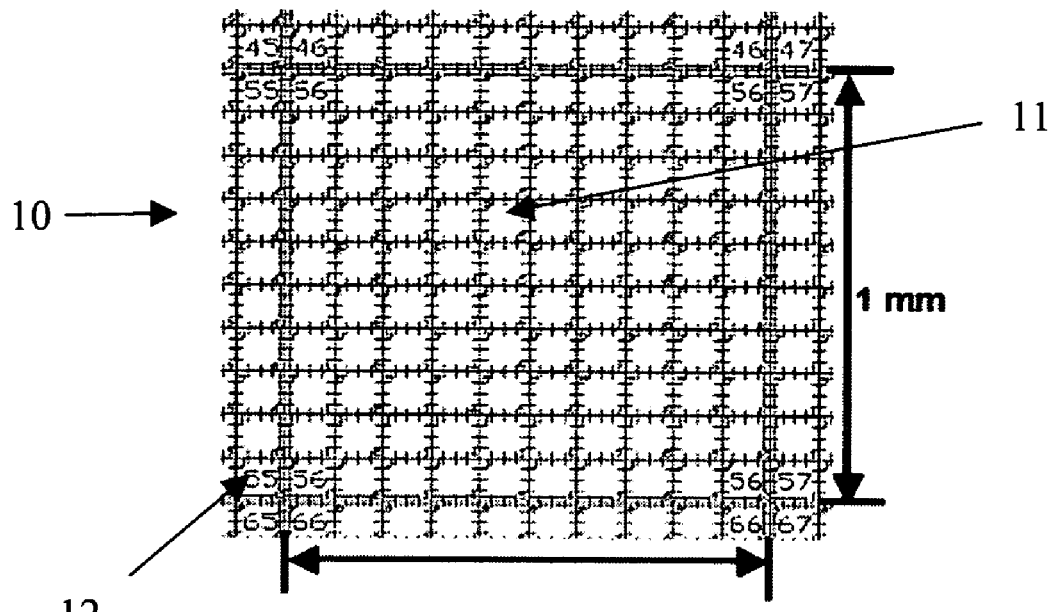
FIGS. 1(a) and 1(b) are design drawings of a micro-pattern embedded optical film.
Figure 1B:
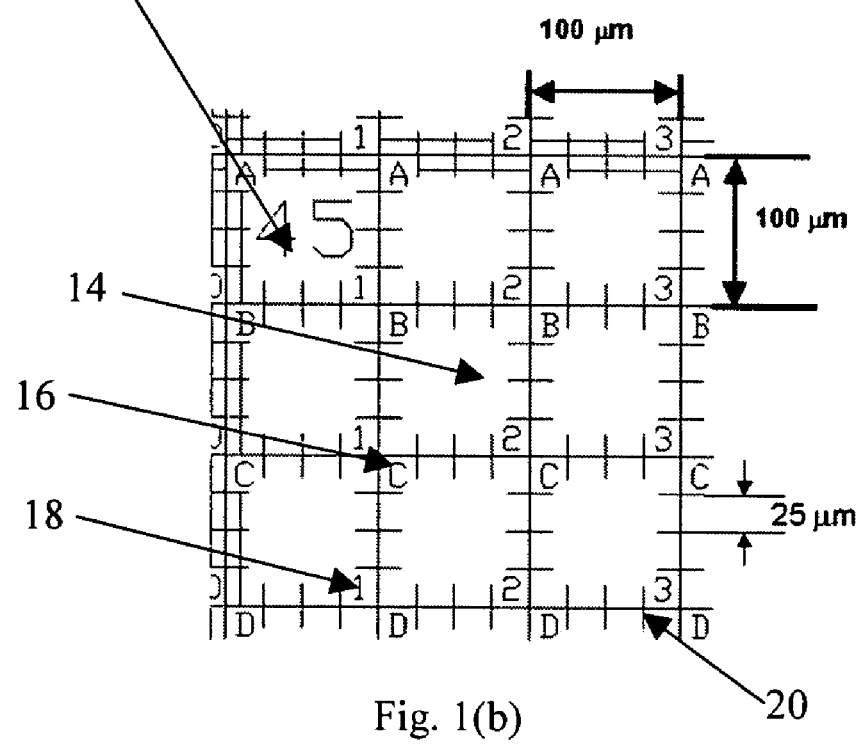

FIGS. 1(a) and 1(b) are design drawings of a micro-pattern embedded plastic optical film (10). Optical film (10) consists of repeating units of square regions (11), which have dimensions of 1 mm×1 mm. The regions (11) are numbered sequentially. Each of the regions (11) is identified by a unique number (12). Within every region (11), there are 100 small squares (14) that are 100 μm×100 μm in size. The small squares (14) are arranged in 10 columns and 10 rows within the region (11). Each row (16) of small squares (14) is labeled from A to J, and each column (18) is labeled from 1 to 10. Within a small square (14), tick marks (20) are 25 μm apart. This design allows identification and direct measurement of majority of mammalian cells, which range from 10 to 100 micrometers in size.

Figure 2A:
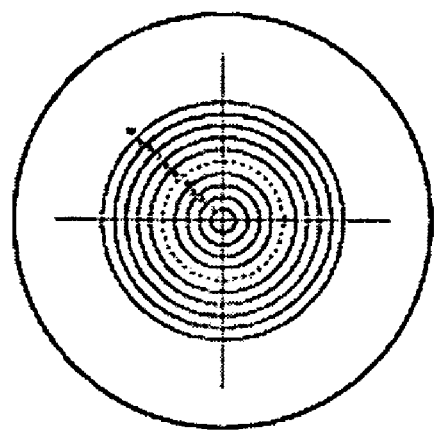
FIGS. 2(a) to 2(c) are illustrative examples of micro-pattern embedded optical film.
Figure 2B:
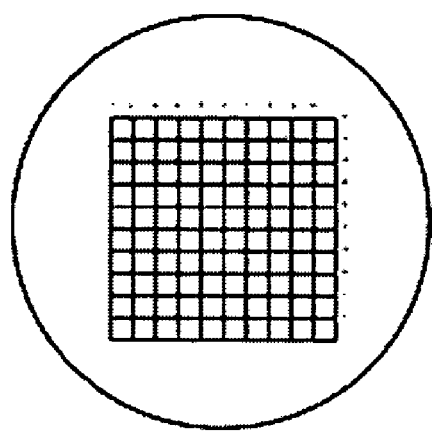
Figure 2C:
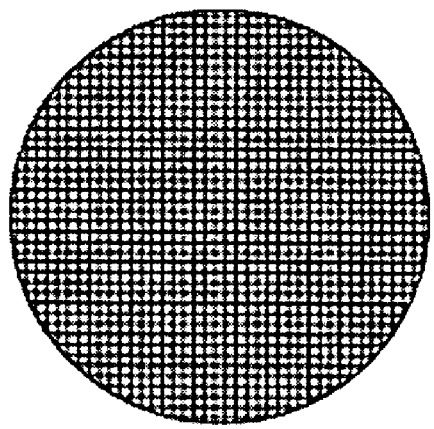
Figure 3A:
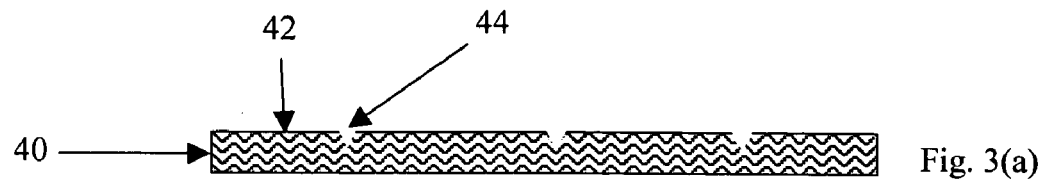
FIGS. 3(a) to 3(d) are cross-section views of micro-pattern embedded optical films.
Figure 3B:
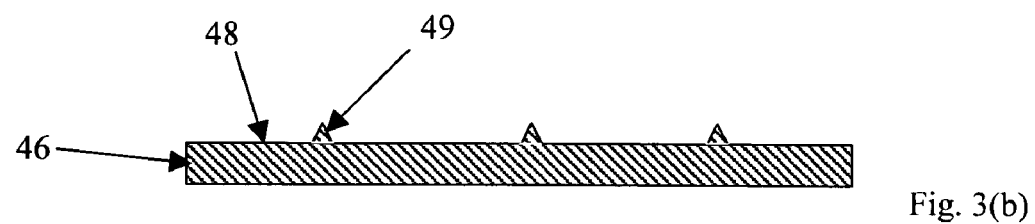
Figure 3C:
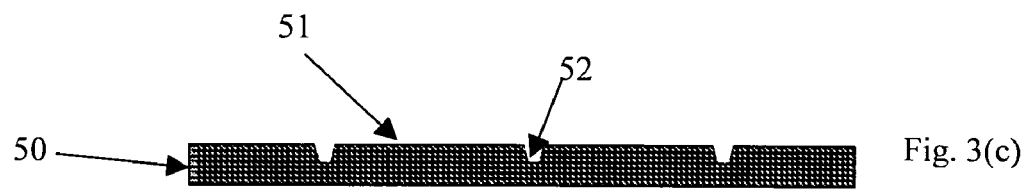
Figure 3D:
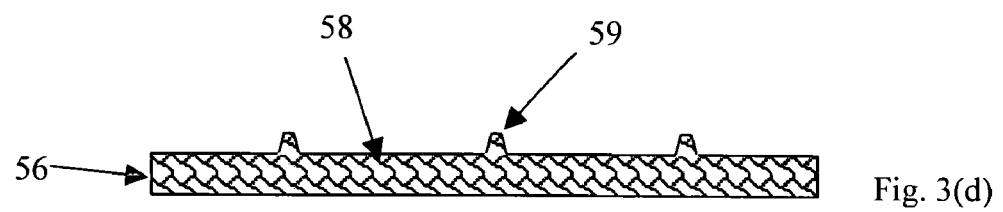

FIGS. 2(a) to 2(c) are illustrative examples of micro-patterns for micro-pattern embedded plastic optical film. Any pattern that is used for microscopy can be incorporated in the optical film.

The purpose of the microscopic lines and features that form the micro-pattern embedded plastic optical film is to create sufficient optical contrast under the same microscope settings as used to observe and to measure cells. It is preferred that the depth of the lines and features in the pattern do not interfere with cell attachment and spreading. It is preferred that the depth is less than 500 μm. It is further preferred the depth is less than 10 μm. It is most preferred that the depth is ranging from 0.1 μm to 1 μm.

The cross-sections of lines forming the micro-patterns may have various geometric shapes. The contrast forming features can be a recess or a surface protrusion.

FIGS. 3(a) to 3(d) are cross-section views of micro-pattern embedded plastic optical films. In one embodiment shown in FIG. 3(a), the surface of a micro-pattern embedded film 40 consists of flat land areas 42 and recessed areas 44. The shapes of the recessed areas 44 are triangles. In another embodiment FIG. 3(b), the surface of a micro-pattern embedded film 46 consists of land areas 48 and protrusions 49. The shapes of protrusions 49 are triangles. In a further embodiment shown in FIG. 3(c), the surface of micro-pattern embedded film 50 consists of land areas 51 and recessed areas 52, wherein the recessed areas 52 have the shapes of trapezoids. In yet another embodiment depicted in FIG. 3(d), the surface of micro-pattern embedded film 56 consists of land areas 58 and protrusions 59, wherein the protrusions are trapezoid-shaped.

Figure 4:
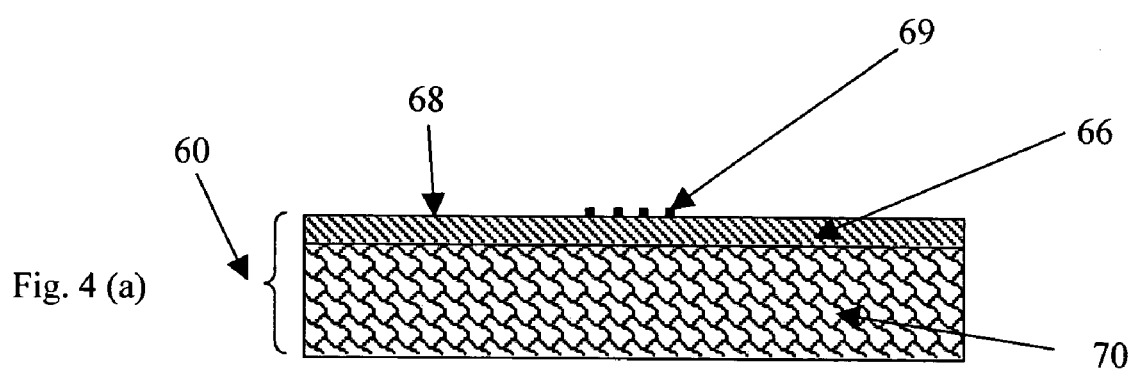
FIGS. 4(a)-4(b) are cross-section views of two configurations of micro-pattern embedded optical film.
Figure 4:
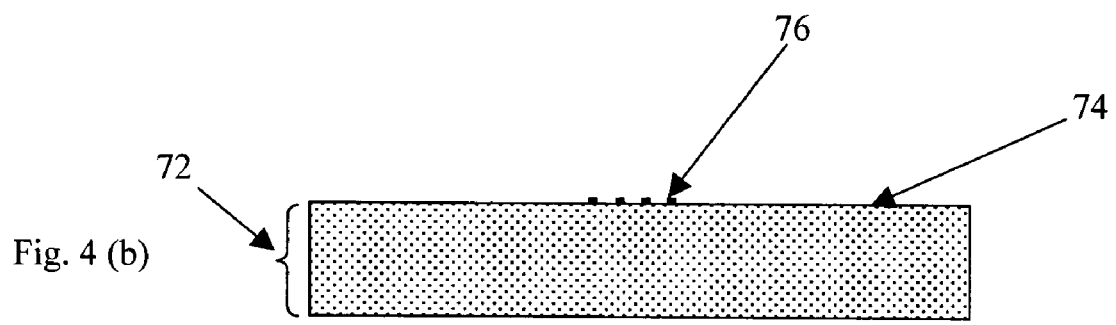

FIG. 4(a) is a schematic drawing of a cross-section view of a micro-pattern embedded film 60 that comprises of a base film 70, a micro-pattern layer 66. The micro-pattern layer 66 consists of land areas 68 and micro-pattern lines 69. FIG. 4(b) is a schematic drawing of a cross-section view of a micro-pattern embedded film 72 that comprises of land areas 74 and micro-pattern lines 76.

Figure 5:
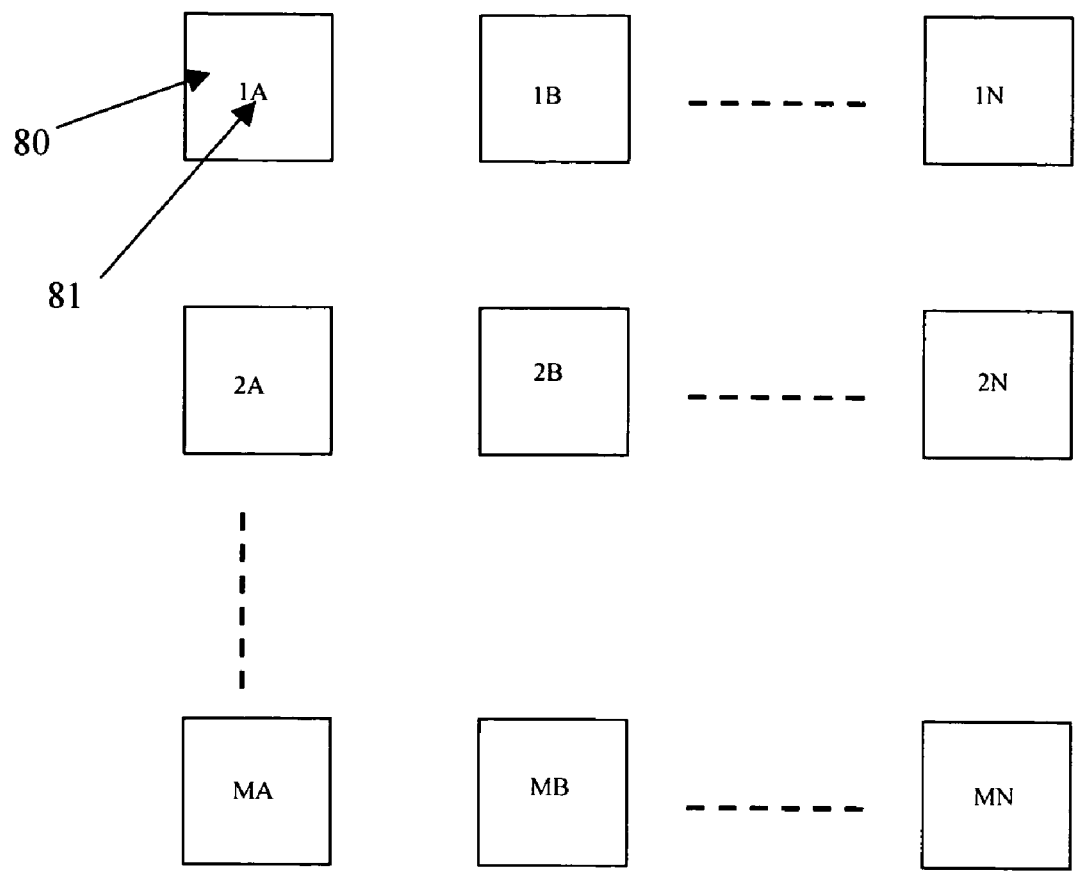
FIGS. 5(a) and 5(b) illustrate a labeling system for a micro-pattern embedded optical film.
Figure 5:
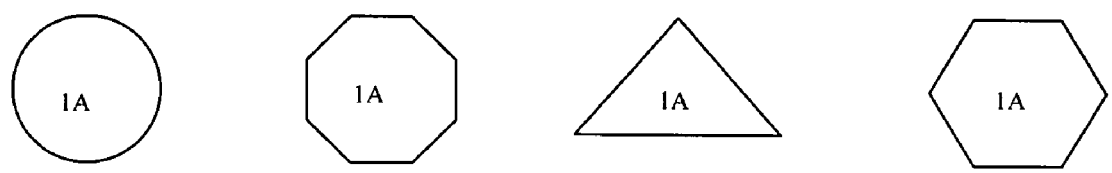

FIG. 5(a) illustrates a labeling system for regions on a micro-pattern embedded film. Each region 80 on the micro-pattern embedded film is identified with a unique label 81. The naming convention of labels 81 is in a predictable fashion, for instance sequentially, to allow easy user navigation. The shapes of the regions 80 may be various geometric shapes, as illustrated in FIG. 5(b).

The thickness of the micro-pattern embedded optical film is chosen to enable measurement of cells under an optical microscope. It is preferred to have the total thickness of the optical film to be less than 3 mm. It is further preferred to have the total thickness to be less than 0.5 mm. It is most preferred to have a total thickness ranging from 50 µm to 250 µm.

Method of Making Micro-Pattern Embedded Optical Film

Creation of microscopic features in plastic material from a molding surface has been described in the prior art. Process of making optical disks with microscopic features using photo-polymerizable materials is disclosed in U.S. Pat. No. 4,374,077. Microstructure-bearing composite plastic articles and method of making said articles are disclosed in U.S. Pat. No. 5,175,030. Grid lines directly molded onto the plastic for cell counting is disclosed in U.S. Pat. No. 4,997,266. Another method called hot stamping or embossing has been used to create holographic films. In the embossing process, a plastic film is pressed against a heated negative molding surface. The plastic in contact with the tool is hot enough to flow, filling the cavities on the surface of the tool. Upon cooling, the plastic film is removed from the tool, bearing features that are negative topography of the mold. A variation of the embossing method is to melt the plastic and cast it onto a tool with a negative molding surface.

The tool that provides the negative molding surface can be made from polymeric, metallic, composite, or ceramic materials. In some instances, the polymerizable material may be cured by radiation being applied through the tool. In such instances, the tool should be sufficiently transparent to permit irradiation of the polymerizable material. For features that are in the range of smaller than 50 micrometer, photolithographic methods can be used to define the features. With this method, a uniform layer of photo-sensitive material is coated onto a surface. Certain areas of the photo-sensitive material is exposed to light and later removed from the surface. In some cases, the patterned photo-sensitive material is adequate as a tool. In other cases, a chemical etching process is applied to remove part of the underlying etchable surface that is not protected by the photo-sensitive material. After etching, the whole area is stripped of the photo-sensitive material, exposing the surface pattern formed on the underlying etchable material.

Illustrative examples of the photo-sensitive material are photoresists commonly used in semiconductor processing. The etchable material can be a metal, such as Al, Cu, Cr, or other materials used for fabricating photomask, such as ion oxide, aluminum oxide. The etchable material can also be inorganic sheets or films, such as $SiO_2$, $Si_3N_4$, $TiO_2$. The etchable material can also be glass.

EXAMPLE 1

Making Micro-Pattern Embedded Optical Film

The micro-pattern embedded plastic optical film consists of two layers. The base substrate is a 10-mil (namely, 0.010 inch thick) polycarbonate film: DE 1-1D Makrofo polycarbonate Gloss/Gloss with liners (Tekra Co., New Berlin, Wis.). The second layer is a clear plastic with micro-pattern formed on its surface.

The process of fabricating the micro-pattern embedded film consists of the following steps.

1. Make a master tool that has a negative image of FIG. 1.
2. Prepare a UV polymerizable solution. (Ex. Lens bond, SK-9 from Summers Optical, Hatfield, Pa.)
3. Cast the UV polymerizable solution between the base substrate and the master tool.
4. Expose the assembly made in step 3 with UV light, resulting in a film with micro-pattern embedded on its surface.
5. Remove the micro-pattern embedded plastic optical film from the master tool.

Steps 3 to 5 may be repeated to produce multiple micro-pattern embedded plastic optical films.

Figure 6:
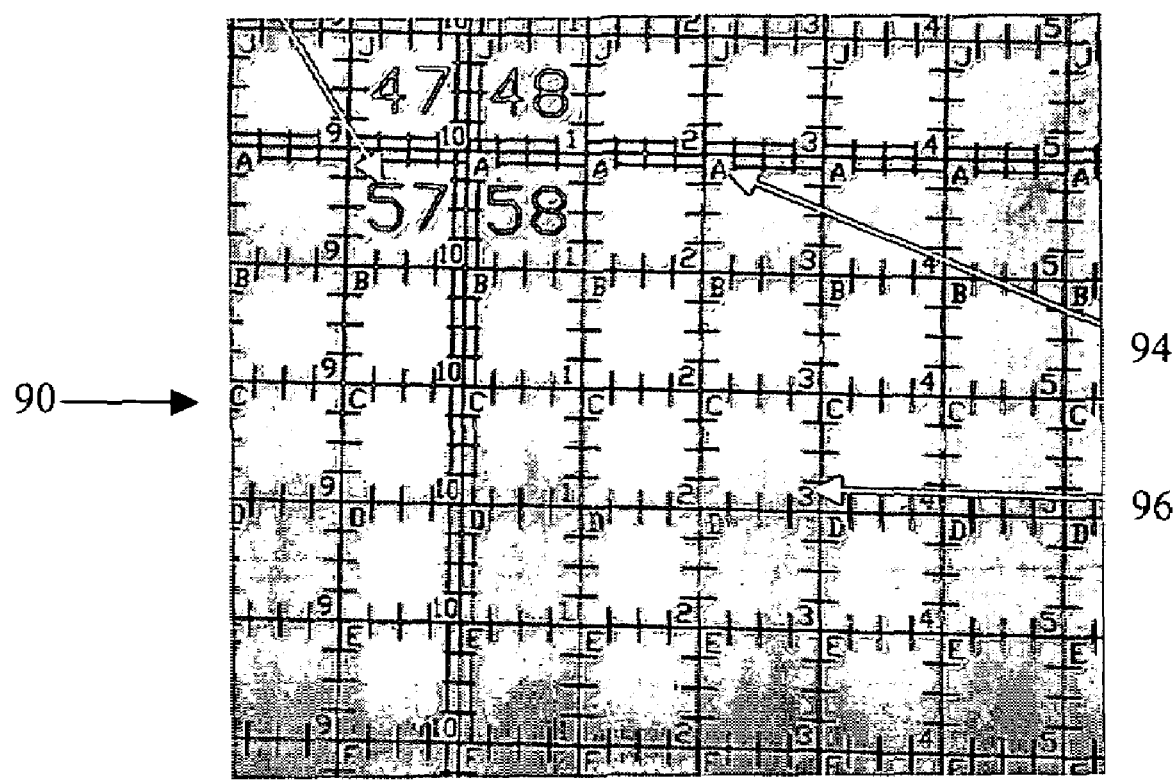
FIG. 6 is a phase contrast image of a micro-pattern embedded optical film.

FIG. 6 is a phase contrast optical image of a micro-pattern embedded optical film 90. Regions are identified by unique identification numbers 92. Also shown are row identification letters 94 and column identification numbers 96.

EXAMPLE 2

Cell Culture on Micro-Pattern Embedded Optical Film

Figure 7:
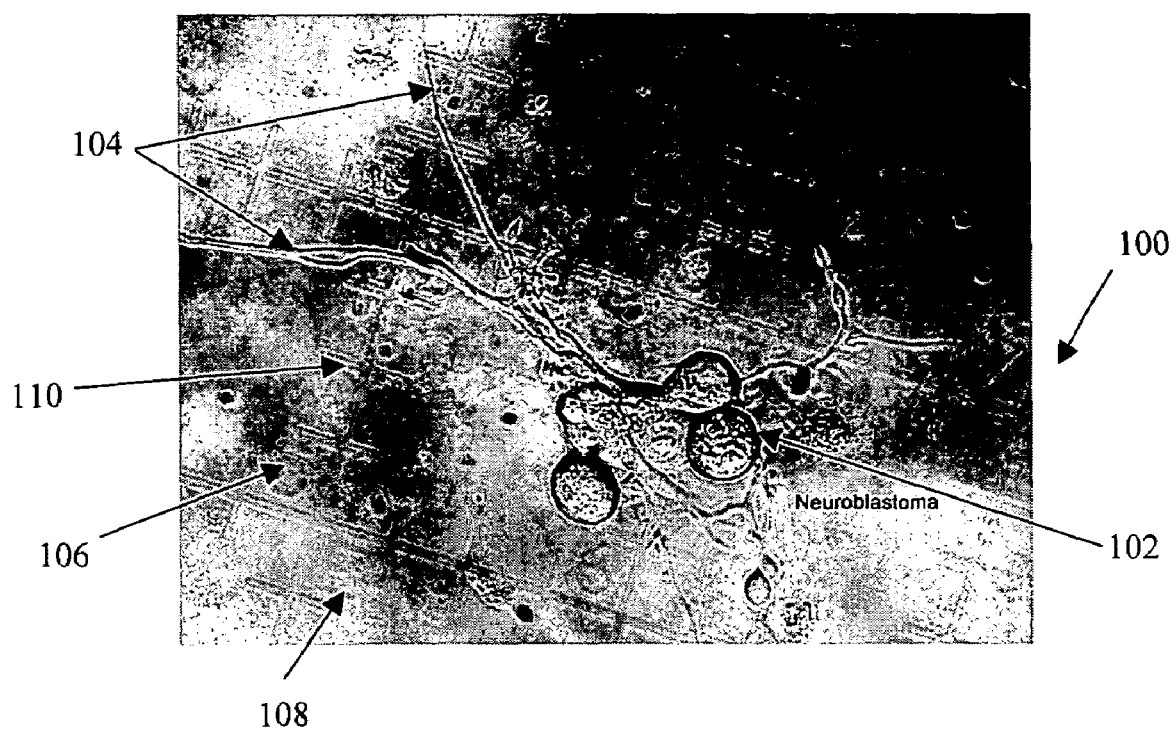
FIG. 7 is a phase contrast image of a cluster of Neuroblastoma cells cultured on a micro-pattern embedded optical film.

The micro-pattern embedded film was placed in a cell culture dish and illuminated by UV light over night in a tissue culture hood for sterilization. Neuroblastoma (CCL-131 from American Type Culture Collection, Manassas, Va.) was cultured following standard protocols. FIG. 7 is a phase contrast image of a cluster of Neuroblastoma cells 102 cultured on a micro-patterned optical film 100. Cell growth 104 is observed. Shown in FIG. 7 are a column identification number 106 and a row identification letter 108. Tick marks 110 are also visible.

Cell-Based Assay Device with Micro-Pattern Embedded Optical Film

Figure 8:
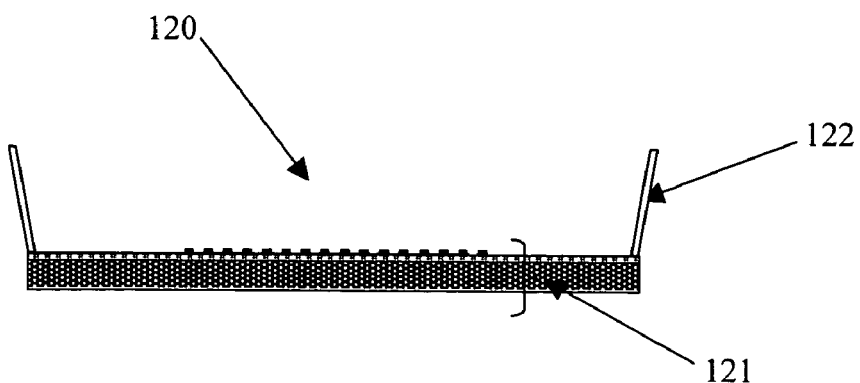
FIGS. 8 (a)-8(d) illustrate a cell-based assay device containing micro-pattern embedded optical film and an assay strategy of using such device.
Figure 8:
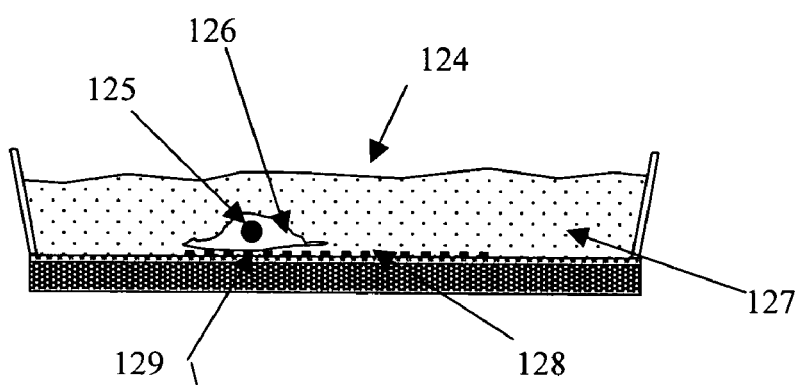
Figure 8:
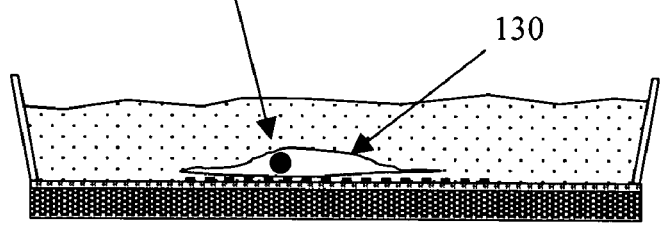
Figure 8:
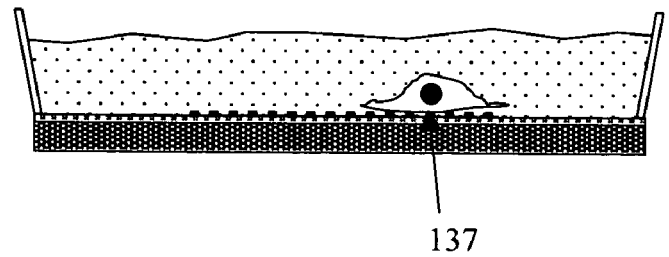

One embodiment of the present invention is a cell assay device 120 with micro-pattern embedded plastic optical film 121, as shown in FIG. 8a. The micro-pattern embedded plastic optical film 121 provides a surface for identification and measurement of cells, while a supporting component 122 provides mechanical strength for handling. The supporting component 122 also functions as a liquid holding part. The height of the supporting component 122 is determined by the amount of liquid sufficient for cell culture media and reagent.

There are multiple possible methods for using the cell assay device with micro-patterns. As an example, one strategy for cell motility assay consists of the following steps, referring to FIG. 8b to FIG. 8d.

Step 1: Seed cells in device 124. Fill device 124 with growth media 127. Allow cell 126 to attach onto surface 128. (FIG. 8b)

Step 2: observe under phase contrast microscope and identify cell 125 for observation.

Step 3: record the location 129 and the initial shape 126 of cell 125. (FIG. 8b)

Step 4: repeat Step 3 for multiple cells.

Step 5: stimulate the cells with reagent of interest by adding reagent into 124 and incubate in an incubator.

Step 6: observe under phase contrast microscope to find location 129 and to find cell 125 (FIG. 8c).

Step 7: record cell shape 130 for cell 125 (FIG. 8c) and record location 137 (FIG. 8d).

Step 8: place device 124 in an incubator.

Step 9: return to Step 6 to obtain data for multiple time points.

The change of morphology for cell 125 is determined by comparing the initial recording of cell shape 126 and the second recording of cell shape 130. The movement of cell 125 is determined by the difference between the initial cell location 129 and the second cell location 137.

Figure 9:
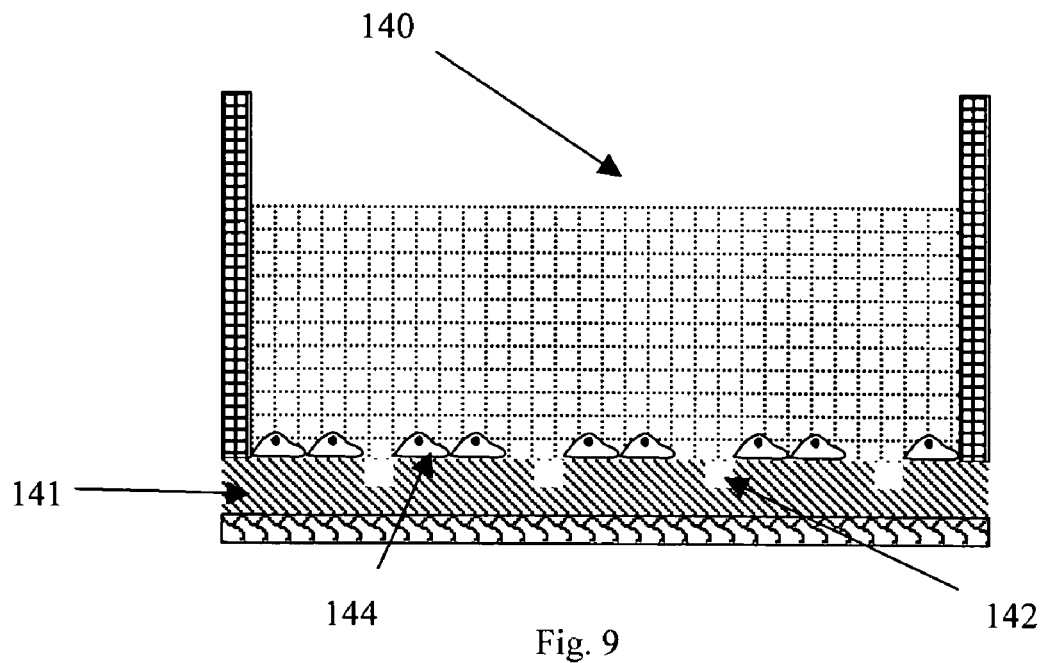
FIG. 9 is a schematic drawing of a cell assay device comprising a micro-pattern embedded optical film as the cell growth surface. Cells grow on the surface with micro-patterns.

FIG. 9 is a schematic drawing of a cell assay device 140 with micro-pattern embedded plastic optical film 141 where pattern 142 is on the cell-contacting surface 144.

Figure 10:
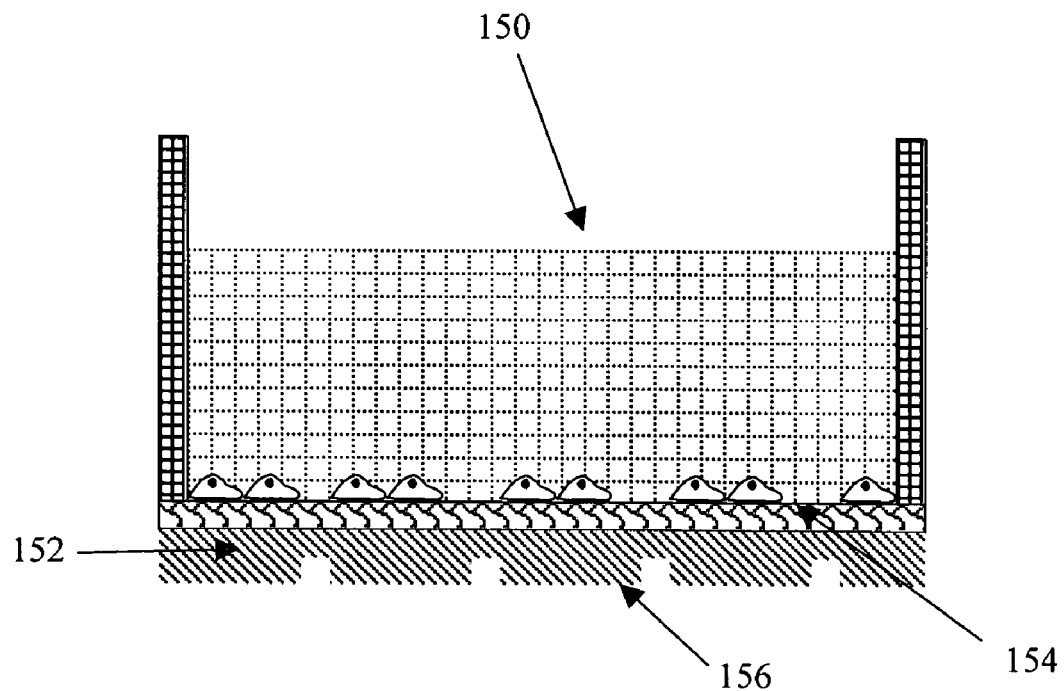
FIG. 10 is a schematic drawing of a cell assay device with a micro-pattern embedded optical film. Cells grow on the flat surface without micro-patterns.

FIG. 10 is a schematic drawing of a cell assay device 150 with micro-pattern embedded plastic optical film 152. The pattern 156 is on the opposing side of the cell-contact surface 154. In this case, cells contact the flat surface 154. To locate an individual cell, the microscope is first focused on the micro-pattern surface 156. After moving to the desired location guided by micro-patterns on the surface 156, the microscope is re-focused to the cell attaching surface 154 for observation and data recording.

Figure 11:
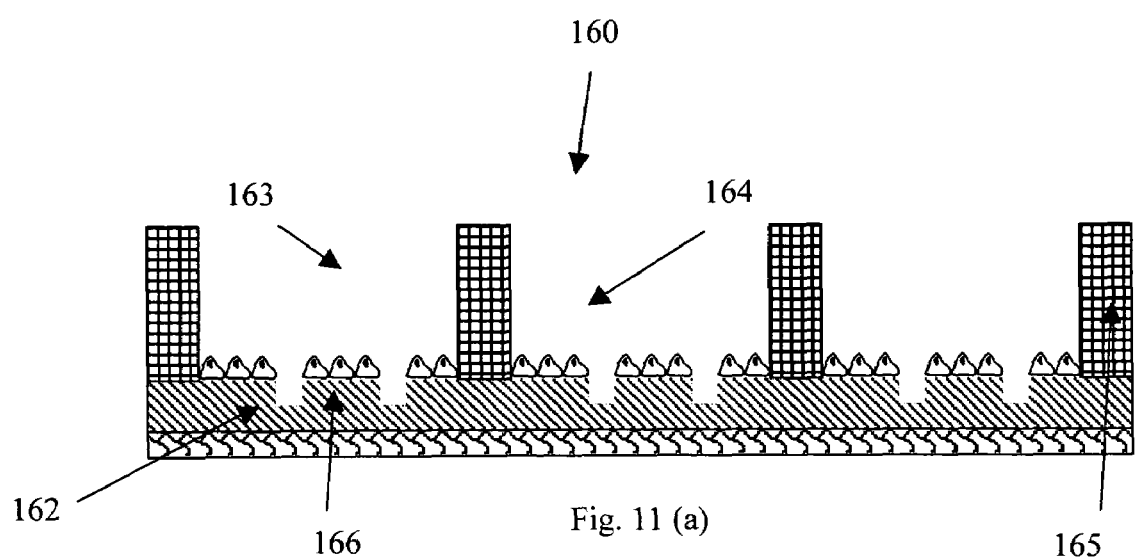
FIGS. 11(a)-11(c) illustrate a cell assay device with multiple assay locations that comprises of a micro-pattern embedded optical film.
Figure 11:
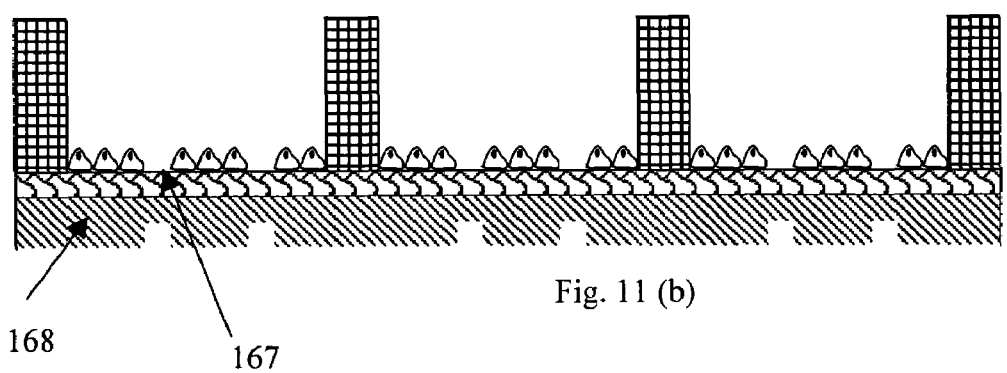
Figure 11:
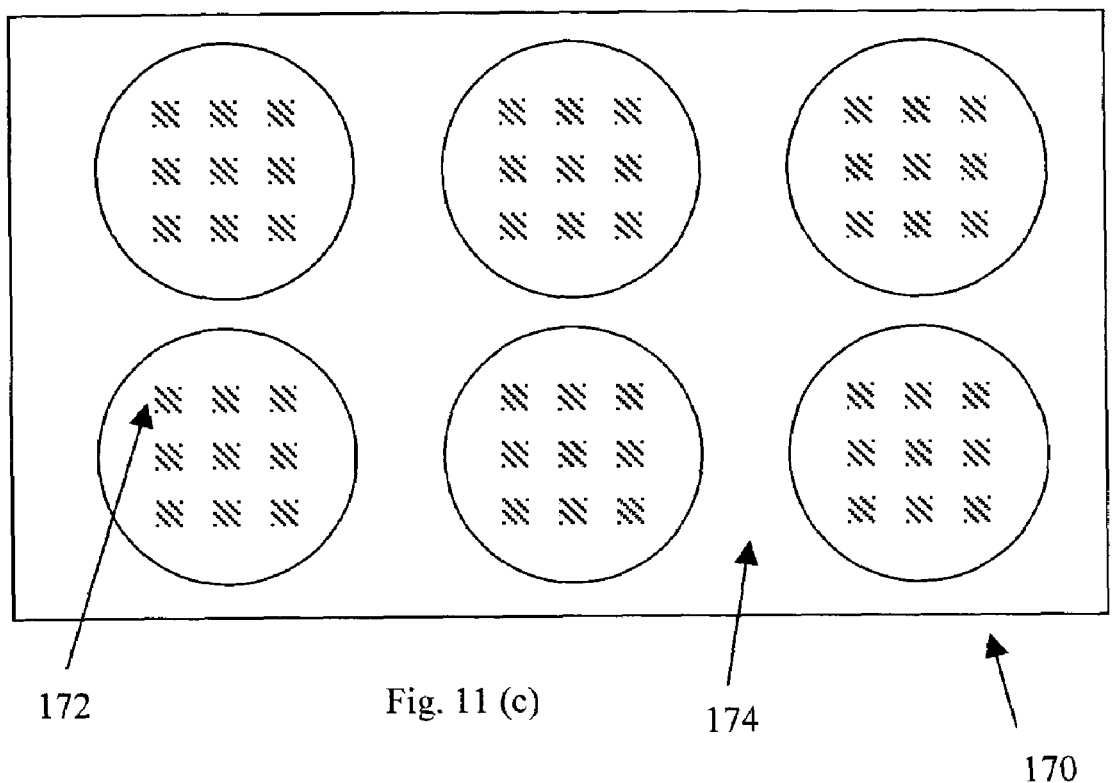

FIG. 11a is a schematic diagram of an assay device 160 with a liquid holding component 165, which comprises of multiple separated compartments 163 and 164. The micro-pattern embedded optical film 162 is in single piece. The liquid holding part 165 completely separates 163 from 164. Device 160 has the micro-pattern embedded surface 166 as the cell-contacting surface. In another embodiment shown in FIG. 11b, the cell-contacting surface 167 is the flat surface of the micro-pattern embedded film 168.

FIG. 11c is a top view of a micro-pattern embedded cell assay device 170. The assay device 170 contains multiple wells 172 for performing separate assays. The multiple wells 172 are separated by the liquid holding component 174.

Figure 12:
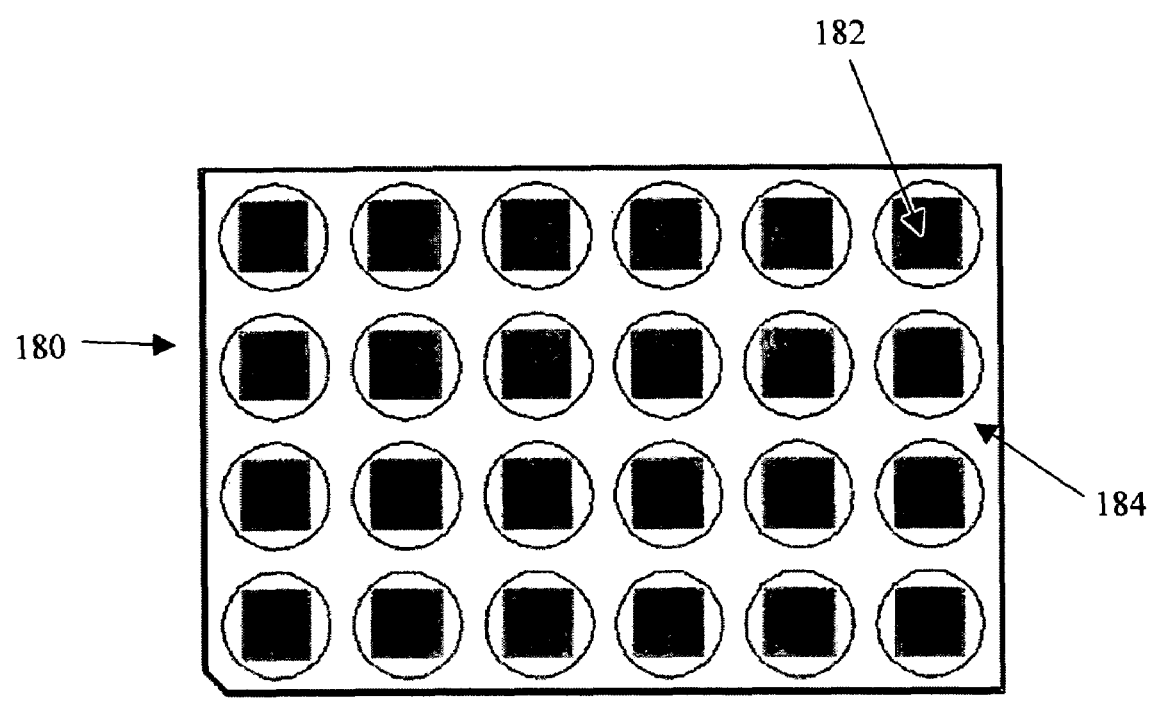
FIG. 12 is a top view of a 24-well micro-pattern embedded cell assay plate.

FIG. 12 is a top view of a 24-well micro-pattern embedded cell assay plate 180. It consists of 24 micro-patterned areas 182. The liquid holding component 184 separates the 24 micro-patterned areas into 24 individual assay devices.

EXAMPLE 3

Cell Culture on a 24-Well Micro-Pattern Embedded Assay Device

Figure 13:
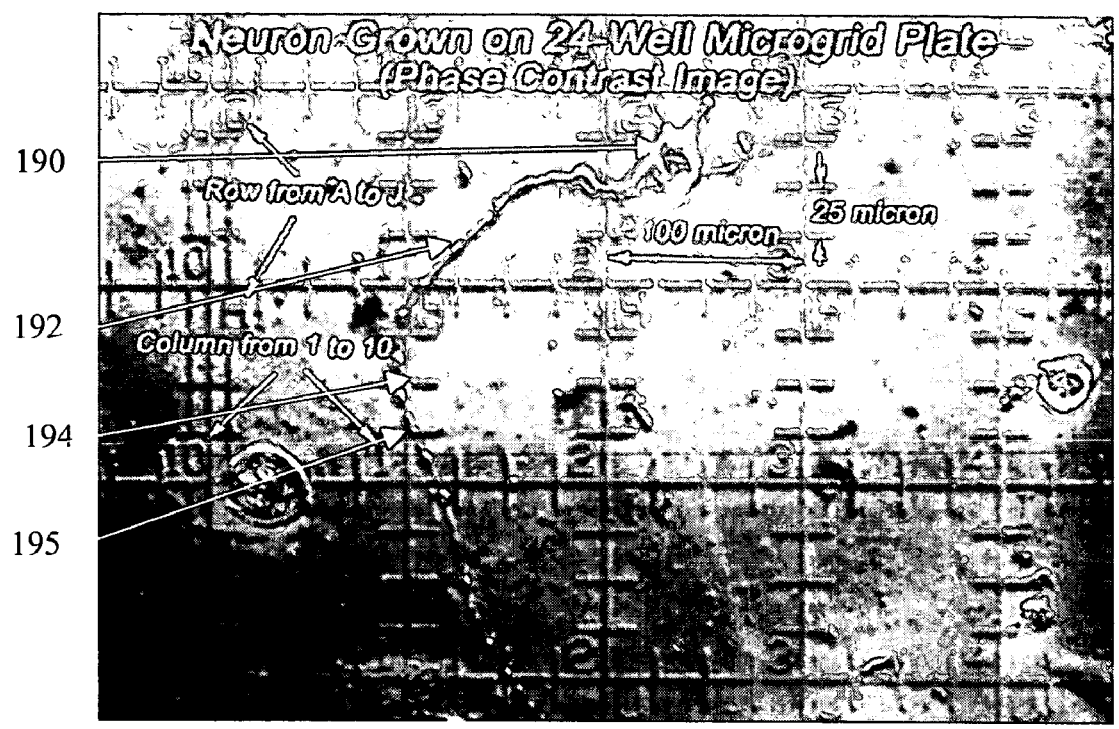
FIG. 13 is a phase contrast image of Neuronblastoma cell cultured on a 24-well micro-pattern embedded cell assay plate.

A 24-well micro-pattern embedded cell assay plate 180 was placed in a tissue culture hood, illuminated by UV light over night for sterilization. Neuroblastoma cells (CCL-131 from American Type Culture Collection, Manassas, Va.) were cultured following standard protocols. FIG. 13 is a phase contrast image of the Neuronblastoma cells on one of the 24 wells. The cell body 190 and axon 192 are clearly visible in the image. Tick marks 194 and 195 are 25 μm apart. The tick marks are used to directly estimate the length of the axon.

Method of Making a Micro-Pattern Embedded Assay Device

The micro-pattern embedded plastic optical film can be attached to the liquid handling component by various methods. The requirements on the attachment material are to provide sufficient mechanical strength to hold the parts together, and not to release materials into the cell culture media during experiments.

FIG. 14 illustrates a method of making a micro-patterned embedded assay device using UV curable bonding materials, with the following steps.

1. Apply the UV curable bonding solution 302 on a flat sheet 304, which serve as and is referred to as a transfer block.
2. Spread the UV curable bonding solution 302 throughout the transfer block 304 into a thin layer 308 with a knife like spreading device 306.
3. Contact the liquid holding part 300 to the transfer block 304.
4. Remove the liquid holding part 311 from the transfer block 304. Some of the UV curable bonding solution 310 is attached onto the liquid holding part 300 to form assembly 311.
5. Contact assembly 311 with micro-pattern embedded film 312 and hold in place to form assembly 316.
6. Apply UV light from source 318 to the assembly 316.
7. Remove UV light.

In a preferred embodiment, the liquid holding component is a bottomless 24 well plate manufactured by Greiner Bio One Inc.

In another embodiment, the liquid holding part is of a height-forming material other than standard polystyrene injection molded parts.

Figure 15:
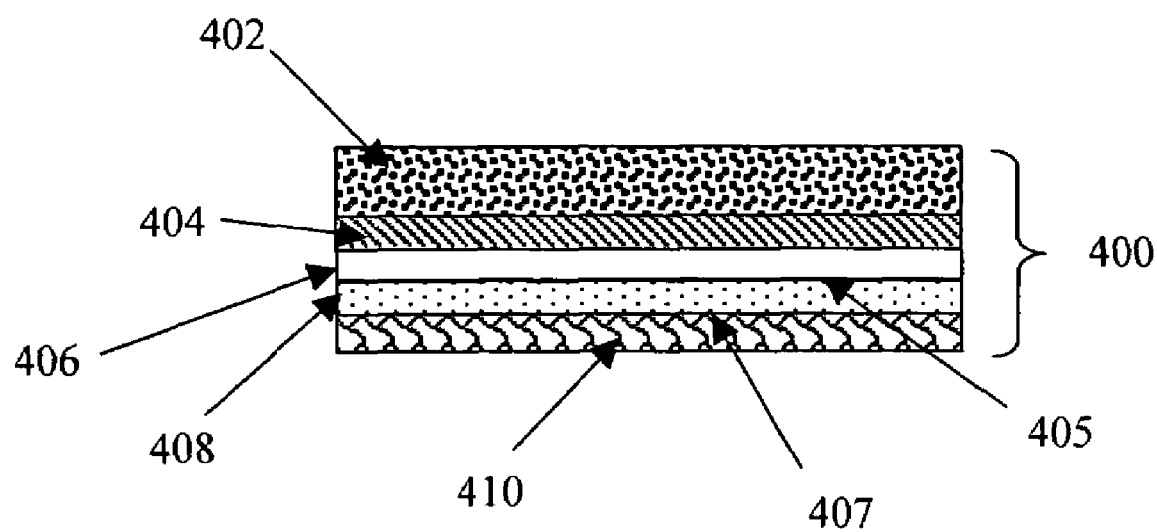
FIGS. 15(a)-15(f) are schematic drawings of a liquid handling part containing height-forming material and a cell assay device with a micro-pattern embedded optical film.

FIG. 15 refers to a liquid holding part 400, comprising of a height-forming layer 402 and a strength layer 406. Layers 402 and 406 are bonded together by an adhesive layer 404. Another layer of pressure sensitive adhesive 408 is applied to the surface 405 of layer 406. The surface 407 of the adhesive 408 is protected by a release liner 410. The strength layer 406 provides mechanical stability required during handling of the device. The process of making a micro-patterned assay device using 400 may comprise the following steps.

1. Cut part 602 and remove it from film 600.
2. Remover release liner 604 to form 608.
3. Attach 608 to micro-pattern embedded film 612.

It is also apparent that during assembly and bonding of the cell assay devices with micro-pattern embedded films, the alignment of various components is important, so that the micro-pattern areas of the films are located at the desired position within cell culture vessels for assay purposes.

Various modifications and alterations of this invention will become apparent to those skilled in the art without departing from the scope and spirit of this invention.

What is claimed is:

1. A device for growth, identification and measurement of cells comprising:
    a micro-pattern embedded plastic optical film having a plurality of regions formed by contrast features on a first side, each of said regions having a unique identifier, each of said contrast features having a depth or a height less than five microns and being observable during microscopic viewing; and
    a supporting component bonded to said first side of said micro-pattern embedded plastic optical film to form, in combination with said micro-pattern embedded plastic optical film, a well having an open top and being configured to receive and hold a liquid having said cells.

2. The device as defined in claim 1, wherein said micro-pattern embedded plastic optical film further comprises a base layer.

3. The device as defined in claim 2 wherein said base layer is a plastic substrate.

4. The device as defined in claim 3 wherein said plastic substrate is a flexible substrate.

5. The device as defined in claim 1, wherein said micro-pattern embedded optical film and said supporting component are bonded by an adhesive layer.

6. The device as defined in claim 5, wherein said adhesive layer comprises a pressure sensitive adhesive.

7. The device as defined in claim 5, wherein said adhesive layer comprises an energy curable adhesive.

8. The device as defined in claim 1, wherein said supporting component has a shape defining a plurality of wells each adapted for performing an assay.

9. The device as defined in claim 1, wherein each of said contrast features has a depth or a height of less than one micron.

10. A device for growth, identification and measurement of cells comprising:
- a micro-pattern embedded plastic optical film having a plurality of regions formed by contrast features on a first side, each of said regions having a unique identifier, each of said contrast features having a depth or a height less than five microns; and
- at least one supporting component attached to said first side of said micro-pattern embedded plastic optical film to form, in combination with said micro-pattern embedded plastic optical film, a plurality of assay locations each having an open top and being configured to receive and hold liquid having said cells, wherein said cells and said contrast features are observable during microscopic viewing without refocusing.

11. The device as defined in claim 10 wherein said at least one supporting component is formed on said micro-pattern embedded plastic optical film using a material deposition technique.

12. The device as defined in claim 10 wherein said at least one supporting component is bonded to said micro-pattern embedded plastic optical film.

13. The device as defined in claim 10, wherein each of said contrast features has a depth or a height of less than one micron.

14. A device for growth, identification and measurement of cells comprising:
- a micro-pattern embedded plastic optical film having a plurality of regions formed by contrast features on a first side, each of said regions having a unique identifier, each of said contrast features being observable during microscopic viewing and having a depth or a height less than a dimension of the cells to allow cell growth and cell mobility across the contrast features; and
- a supporting component bonded to said first side of said micro-pattern embedded plastic optical film to form, in combination with said micro-pattern embedded plastic optical film, a well having an open top and being configured to receive and hold a liquid having said cells.

15. The device as defined in claim 14 wherein a depth or a height of each of said contrast features is less than five microns.

16. The device as defined in claim 14, wherein a depth or a height of each of said contrast features is less than one micron.

* * * * *